US009738931B2

(12) United States Patent
Hahn et al.

(10) Patent No.: US 9,738,931 B2
(45) Date of Patent: *Aug. 22, 2017

(54) NON-INVASIVE DETECTION OF FETAL GENETIC TRAITS

(71) Applicant: SEQUENOM, INC., San Diego, CA (US)

(72) Inventors: Sinuhe Hahn, Liestal (CH); Wolfgang Holzgreve, Basel (CH); Bernhard Zimmermann, Los Angeles, CA (US); Ying Li, Basel (CH)

(73) Assignee: SEQUENOM, INC., San Diego, CA (US)

( * ) Notice: Subject to any disclaimer, the term of this patent is extended or adjusted under 35 U.S.C. 154(b) by 495 days.

This patent is subject to a terminal disclaimer.

(21) Appl. No.: 13/757,637

(22) Filed: Feb. 1, 2013

(65) Prior Publication Data
US 2014/0193808 A1 Jul. 10, 2014

Related U.S. Application Data

(63) Continuation of application No. 13/029,999, filed on Feb. 17, 2011, now abandoned, which is a continuation of application No. 10/964,726, filed on Oct. 15, 2004, now abandoned.

(30) Foreign Application Priority Data

Oct. 16, 2003 (EP) .................................... 03405742

(51) Int. Cl.
C12Q 1/68 (2006.01)
C12P 19/34 (2006.01)
C07H 21/02 (2006.01)

(52) U.S. Cl.
CPC ......... *C12Q 1/6883* (2013.01); *C12Q 1/6806* (2013.01); *C12Q 2600/156* (2013.01)

(58) Field of Classification Search
CPC ............ C12Q 1/6806; C12Q 2565/125; C12Q 1/6883; C12Q 2600/156
See application file for complete search history.

(56) References Cited

U.S. PATENT DOCUMENTS

| 5,674,686 | A | 10/1997 | Schumm et al. |
| 6,258,540 | B1 | 7/2001 | Lo et al. |
| 7,838,647 | B2 | 11/2010 | Hahn |
| 2005/0164241 | A1 | 7/2005 | Hahn |
| 2011/0245482 | A1 | 10/2011 | Hahn et al. |
| 2011/0251076 | A1 | 10/2011 | Hahn |
| 2012/0302741 | A1 | 11/2012 | Hahn |
| 2013/0190483 | A1 | 7/2013 | Hahn et al. |

FOREIGN PATENT DOCUMENTS

| EP | 1524321 | 4/2005 |
| WO | WO 98/39474 | 9/1998 |
| WO | WO 03/074723 | 9/2003 |
| WO | WO 2004/078994 | 8/2004 |
| WO | WO 2004/079011 | 8/2004 |

OTHER PUBLICATIONS

Chiu R.W.K. et al., Clinical Chemistry May 2002 vol. 48 No. 5 778-780.*
Speiser P.W. Am J Pharmacogenomics 2001; 1 (2): 101-110.*
Office Action mailed on Sep. 12, 2013 in U.S. Appl. No. 13/779,300, filed Feb. 27, 2013 and published as US 2013-0190483 on Jul. 25, 2013.
Office Action mailed on Oct. 2, 2013 in U.S. Appl. No. 13/557,025, filed Jul. 24, 2012 and published as US 2012-0302741 on Nov. 29, 2012.
Office Action mailed on Jan. 16, 2014 in U.S. Appl. No. 13/029,995, filed Feb. 17, 2011 and published as US 2011-0251076 on Oct. 13, 2011.
Office Action mailed on Feb. 7, 2014 in U.S. Appl. No. 13/557,025, filed Jul. 24, 2012 and published as US 2012-0302741 on Nov. 29, 2012.
Shimamura et al., "Modulation by Polyamines of DNA-Dependent DNA Polymerase Activity From Human Serum" International Journal of Biochemistry (1990) 22(5):545-549.
Angert, Robert M., "Fetal cell-free plasma DNA concentrations in maternal blood are stable 24 hours after collection: analysis of first- and third-trimester samples," Clinical Chemistry 49, No. 1 2003 pp. 195-198.
Bianchi, "Fetal DNA in maternal plasma: the plot thickens and the placental barrier thins," Am. J. Hum. Genet. 62: 763-764, 1998.
Boom R et al 'Human cytomegalovirus DNA in plasma and serum specimens of renal transplant recipients is highly fragmented.' J Clin Microbiol. Nov. 2002;40(11):4105-4113.
Brownstein MJ et al., "Modulation of non-ternplated nucleotide addition by Taq DNA polymerase: primer modifications that facilitate genotyping." Biotechniques. Jun. 1996;20(6):1004, 1006, 1008-1010.
Chan et al., "Size distributions of maternal and fetal DNA in maternal plasma," Clinical Chemistry, 50, No. 1, 2004, pp. 88-92.
Chiu et al., "Effects of blood-processing protocols on fetal and total DNA quantification in maternal plasma," Clinical Chemistry 47 2001 pp. 1607-1613.
Chungwen W et al 'Screening cell-free fetal DNA in maternal plasma.' Qiagen News, Issue No. 4, 2001, pp. 14-16.

(Continued)

*Primary Examiner* — Stephen Kapushoc
(74) *Attorney, Agent, or Firm* — Grant IP, Inc.

(57) ABSTRACT

Blood plasma of pregnant women contains fetal and (generally >90%) maternal circulatory extracellular DNA. Most of said fetal DNA contains ≤500 base pairs, said maternal DNA having a greater size. Separation of circulatory extracellular DNA of <500 base pairs results in separation of fetal from maternal DNA. A fraction of a blood plasma or serum sample of a pregnant woman containing, due to size separation (e.g. by chromatography, density gradient centrifugation or nanotechnological methods), extracellular DNA substantially comprising ≤500 base pairs is useful for non-invasive detection of fetal genetic traits (including the fetal RhD gene in pregnancies at risk for HDN; fetal Y chromosome-specific sequences in pregnancies at risk for X chromosome-linked disorders; chromosomal aberrations; hereditary Mendelian genetic disorders and corresponding genetic markers; and traits decisive for paternity determination) by e.g. PCR, ligand chain reaction or probe hybridization techniques, or nucleic acid arrays.

14 Claims, No Drawings

(56) References Cited

OTHER PUBLICATIONS

Du, Ming et al., "Rapid Separation and laser-induced fluorescence detection of mutated DNA by capillary electrophoresis in a self-coating, low-viscosity polymer matrix", Electrophoresis, Sep. 2003,24(18), pp. 3147-3153.
Erba et al., "Structure, Chromosome Location and Expression of the Human Y-Actin Gene: Differential Evolution, Location and Expression of the Cytoskeletal b- and y Actin Genes", Molecular and Cellular Biology, 8(4): pp. 1775-1789.
Fan et al., "Analysis of the size distributions of fetal and maternal cell-free DNA by paired-end sequencing," Clinical Chemistry 56:8, 1-8, (2010).
Ganshert-Ahlert et al., "Three cases of 45,X/46, Xynf mosaicism: Molecular Analysis revealed heterogeneity of the nonfluorescent Y chromosome," Human Genetics (1987), 76:pp. 153-156.
Ganshirt-Ahlert D et al 'Ratio of fetal to maternal DNA is less than 1 in 5000 at different gestational ages in maternal blood.' Clin Genet. Jul. 1990;38(1):38-43.
Giacona et al., "Cell-free DNA in human blood plasma: length measurements in patients with pancreatic cancer and healthy controls," Pancreas 17, No. 1, 1998, p. 89-97.
Gosse et al., "Initial degradation of deoxyribonucleic acid after injection in mammals," Cancer Research (Jul. 1965) vol. 25, p. 877-883.
Hahn et al. Both maternal and fetal cell-free DNA in plasma fluctuate. Ann N Y Acad Sci 2001:141-144.
Hahn, S. et al., "Multiplex and Real-Time Quantitative PCR on Fetal DNA in Maternal Plasma, A Comparison with Fetal Cells Isolated from Maternal Blood," Annals of the New York Academy of Sciences, New York Academy of Sciences, New York, NY, vol. 906,2000, pp. 148-152.
Han, Jongyoon et al., "Characterization and Optimization of an Entropic Trap for DNA Separation", Analytical Chemistry, vol. 74, No. 2, Jan. 15, 2002, pp. 394-401.
Hecker, Karl H. et al., "Analysis and purification of nucleic acids by ion-pair reversed-phase high-performance liquid chrornatography", J. Biochem. Biophys. Methods, Nov. 20, 2000,46(1-2), pp. 83-93.
Houfflin-Debarge, Veronique et al., "High sensitivity of fetal DNA in plasma compared to serum and nucleated cells using unnested PCR in maternal blood", Fetal Diagnosis and Therapy, vol. 15, No. 2, Mar. 2000, pp. 102-107.
Hulten et al., "Rapid and simple prenatal diagnosis of common chromosome disorders: advantages and disadvantages of the molecular methods FISH and QF-PCR," Reproduction (2003) 126, 279-297.
Huppertz et al., "Villous cytotrophoblast regulation of the syncytial apoptotic cascade in the human placenta," Histochem Chem Biol 110, 1998, p. 495-508.
Kolialexi et al., "Apoptosis in maternal peripheral blood during pregnancy," Fetal Diagn Ther 16, 2001, p. 32-37.
Levenson. "The Road to Better Down Syndrome Screening, Will Fetal Nucleic Acids Someday Provide Safer Answers?," Clinical Laboratory News May 2007 vol. 33, No. 5.
Li et al. (2004), "Size Separation of Circulatory DNA in Maternal Plasma Permits Ready Detection of Fetal DNA Polymorphisms." Clinical Chemistry, 50(6): pp. 1002-1022.
Li et al., "Cell-free DNA in maternal plasma: is it all a question of size?," Annals NY Acad Sci, 1075, 2006, p. 81-87.
Lin et al., "Selective extraction of size-fractioned DNA samples in microfabricated electrophoresis devices", Journal of CImOMATOGRAPHY A., Aug. 29, 2003, 1010(2), pp. 255-268.
Liu et al., "Circulating DNA in plasma and serum: Biology, preanalytical issues and diagnostic applications," Clinical Chemistry and Laboratory Medicine vol. 40 Issue 10 2002 pp. 962-968.
Lo et al, "Prenatal diagnosis: progress through plasma nucleic acids," Nature Reviews Genetics 8, 71-77 (Jan. 2007).
Lo et al., "Digital PCR for the Molecular detection of fetal chromosomal aneuploidy," PNAS USA vol. 104, No. 32, 13116-13121.
Lo et al., "Maternal Plasma DNA Sequencing Reveals the Genome-Wide Genetic and Mutational Profile of the Fetus," Science Translational Medicine, vol. 2, Issue 61, 1-13, Dec. 8, 2010.
Lo et al., "Plasma placental RNA allelic ration permits noninvasive prenatal chromosomal aneuploidy detection," Nature Medicine vol. 13, No. 2, Feb. 2007, 218-222.
Lo et al., "Prenatal diagnosis of fetal RhD status by molecular analysis of maternal plasma," NEJM 339, No. 24, 1998, p. 1734-1738.
Lo et al., "Quantitative analysis of fetal DNA in maternal plasma and serum: implications for noninvasive prenatal diagnosis," Am. J. Hum. Genet. 62: 768-775, 1998.
Lo et al., "Free Fetal DNA in Maternal Circulation" JAMA Dec. 15, 2004; (23) 2835.
Lo, "Fetal nucleic acids in maternal plasma," Ann. N.Y. Acad. Sci. 1137:140-143 (2008).
Lo, Y. M. D. et al.., "Presence of Fetal DNA in Maternal Plasma and Serum", Lancet, vol. 350, Aug. 16, 1997, pp. 485-487.
Lo, Y. M. Dennis, "Fetal DNA in maternal plasma: Biology and diagnostic applications", Clinical Chemistry, American Association for Clinical Chemistry, vol. 46, No. 12, Dec. 2000, pp. 1903-1906.
Opposition to European Patent No. 1 524 321 B1, Titled: "Non-Invasive Detection of Fetal Genetic Traits", Received by at the EPO on Apr. 1, 2010.
Pelling et al., "A Human Genomic Library Enriched in Transcriptionally Active Sequences (aDNA Library)", Genome Research, 2000, 10:874-886.
Pertl, Barbara et al., "Fetal DNA in maternal plasma: Emerging clinical applications", Obstetrics and Gynecology, vol. 98, No. 3, Sep. 2001, pp. 483-490.
Pertl, Barbara et at., "Detection of male and female fetal DNA in maternal plasma by multiplex fluorescent polymerase chain reaction amplification of short tandem repeats", Human Genetics, vol. 106, No. I, Jan. 2000, pp. 45-46.
Puers, et al., "Identification of repeat sequence heterogeneity at the polymorphic short tandem repeat locus HUMTH01[AATG]n and reassignment of alleles in population analysis by using a locus-specific allelic ladder," Am J. Hum Gent. (1993) v. 53, pp. 953-958.
Raptis et al., "Quantitation and Characterization of Plasma DNA in Normal and Patients with Systemic Lupus Erythematosus", J. Clin. Invest, Dec. 1980, 66(6), pp. 1391-1399.
Roach et al., "Analysis of genetic inheritance in a family quartet by whole genome sequence," Science, Apr. 30, 2010, 328(5978): pp. 636-639.
Siva et al., "Evaluation of the clinical usefulness of isolation of fetal DNA from the maternal circulation", The Australian and New Zealand Journal of Obstetrics & Gynaecology, Australia, Feb. 2003, vol. 43, No. 1, Feb. 2003, pp. 10-15.
Smid et al., "Evaluation of different approaches for fetal DNA analysis from maternal plasma and nucleated blood cells", Clinical Chemistry, vol. 45, No. 8, Sep. 1999, pp. 1570-1572.
Teeters, M.A. et al., "Adsorptive membrane chromatography for purification of plasmid DNA", Journal of Chromatography A, Mar. 7, 2003,989(1), pp. 165-173.
van Wijk et al., Clinical Chemistry 46, No. 5, 2000 pp. 729-731.
Vecchione et al., "Fetal Sex Identification in Maternal Plasma by Means of Short Tandem Repeats on Chromosome X," Ann. N. Y. Acad.Sci. 1137: 148-156 (2008).
Wagner et al., "RHD gene deletion occurred in the Rhesus box" Blood 95(12): pp. 3662-3668 Jun. 15, 2002.
Xu, Feng et al., "Reduced viscosity polymer matrices for microchip electrophoresis of double-stranded DNA", Analyst, Jun. 2003,128(6), pp. 589-592.
Lapaire et al., "Cell-Free Fetal DNA in Amniotic Fluid: Unique Fragmentation Signatures in Euploid and Aneuploid Fetuses," Clinical Chemistry, 53:3, 405-411 (2007).
Pertl et al., "Detection of male and female fetal DAN in maternal plasma by multiplexing fluorescent polymerase chain amplification of short tandem repeats," Hum Genet (2000) 106:45-49.
Jahr S. et al., Cancer Res 2001;61:1659-1665.
Hamprecht et al., Journal of Virological Methods 69 (1997) 125-135.

(56) References Cited

OTHER PUBLICATIONS

Office Action dated: Jan. 25, 2012 in U.S. Appl. No. 10/964,726, filed Oct. 15, 2004 and published as: 2005/0164241 on Jul. 28, 2005.
Office Action dated: Jun. 22, 2011 in U.S. Appl. No. 10/964,726, filed Oct. 15, 2004 and published as: 2005/0164241 on Jul. 28, 2005.
Office Action dated: Oct. 13, 2009 in U.S. Appl. No. 10/964,726, filed Oct. 15, 2004 and published as: 2005/0164241 on Jul. 28, 2005.
Office Action dated: Feb. 4, 2009 in U.S. Appl. No. 10/964,726, filed Oct. 15, 2004 and published as: 2005/0164241 on Jul. 28, 2005.
Office Action dated: Mar. 24, 2008 in U.S. Appl. No. 10/964,726, filed Oct. 15, 2004 and published as: 2005/0164241 on Jul. 28, 2005.
Office Action dated: Jul. 27, 2007 in U.S. Appl. No. 10/964,726, filed Oct. 15, 2004 and published as: 2005/0164241 on Jul. 28, 2005.
Office Action dated: Nov. 15, 2006 in U.S. Appl. No. 10/964,726, filed Oct. 15, 2004 and published as: 2005/0164241 on Jul. 28, 2005.
Office Action dated: Jun. 2, 2006 in U.S. Appl. No. 10/964,726, filed Oct. 15, 2004 and published as: 2005/0164241 on Jul. 28, 2005.
Office Action dated: Sep. 29, 2010 in U.S. Appl. No. 11/855,558, filed Sep. 14, 2007 and issued as: U.S. Pat. No. 7,838,647 on Nov. 23, 2010.
Office Action dated: Mar. 31, 2010 in U.S. Appl. No. 11/855,558, filed Sep. 14, 2007 and issued as: U.S. Pat. No. 7,838,647 on Nov. 23, 2010.
Office Action dated: Oct. 23, 2012 in U.S. Appl. No. 13/029,995, filed Feb. 17, 2011 and published as: 2011/0251076 on Oct. 13, 2011.
Office Action dated: Apr. 13, 2012 in U.S. Appl. No. 13/029,995, filed Feb. 17, 2011 and published as: 2011/0251076 on Oct. 13, 2011.
Office Action dated: Oct. 22, 2012 in U.S. Appl. No. 13/029,999, filed Feb. 17, 2011 and published as: 2011/0245482 on Oct. 6, 2011.
Office Action dated: Apr. 10, 2012 in U.S. Appl. No. 13/029,999, filed Feb. 17, 2011 and published as: 2011/0245482 on Oct. 6, 2011.
Office Action dated: Jan. 30, 2013 in U.S. Appl. No. 13/557,025, filed Jul. 24, 2012 and published as: 2012/0302741 on Nov. 29, 2012.
Office Action dated: Oct. 18, 2012 in U.S. Appl. No. 13/557,025, filed Jul. 24, 2012 and published as: 2012/0302741 on Nov. 29, 2012.
Office Action dated: Sep. 14, 2012 in U.S. Appl. No. 13/557,025, filed Jul. 24, 2012 and published as: 2012/0302741 on Nov. 29, 2012.
Office Action mailed on May 13, 2014 in U.S. Appl. No. 13/779,300, filed Feb. 27, 2013 and published as US 2013-0190483 on Jul. 25, 2013.
Ikeda et al., "Existence frequency of fetal DNA in mother's blood plasma: Difference based on fragment length" Acta Obstetrica et Gynaecologica Japonica, Feb. 2003, vol. 55, No. 2, p. 474 [P-910], Japan Society of Obstetrics and Gynecology.
Office Action mailed on Sep. 8, 2014 in U.S. Appl. No. 13/557,025, filed Jul. 24, 2012 and published as US 2012-0302741 on Nov. 29, 2012.
Office Action mailed on Feb. 13, 2015 in U.S. Appl. No. 13/029,995, filed Feb. 17, 2011 and published as US 2011-0251076 on Oct. 13, 2011.
Office Action mailed on Jun. 8, 2015 in U.S. Appl. No. 13/779,300, filed Feb. 27, 2013 and published as US 2013-0190483 on Jul. 25, 2013.
Office Action mailed on Jul. 8, 2015 in U.S. Appl. No. 13/029,995, filed Feb. 17, 2011 and published as US 2011-0251076 on Oct. 13, 2011.
Office Action mailed on Nov. 17, 2015 in U.S. Appl. No. 13/557,025, filed Jul. 24, 2012 and published as US 2012-0302741 on Nov. 29, 2012.
Lo et al., "Strategies for the detection of autosomal fetal DNA sequence from maternal peripheral blood" Annals of the New York Academy of Sciences (1994) 731:204-225.
Office Action mailed on Jun. 14, 2016 in U.S. Appl. No. 13/779,300, filed Feb. 27, 2013 and published as US 2013-0190483 on Jul. 25, 2013.
Office Action mailed on Dec. 16, 2016 in U.S. Appl. No. 13/029,995, filed Feb. 17, 2011 and published as US 2011-0251076 on Oct. 13, 2011.

* cited by examiner

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
    SRY_Fwd primer

<400> SEQUENCE: 1
tcctcaaaag aaaccgtgca t                                           21

```
<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      SRY_Rev primer

<400> SEQUENCE: 2
agattaatgg ttgctaagga ctggat                                              26

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      FAM labeled TaqMan SRY_MGB probe

<400> SEQUENCE: 3
tccccacaac ctctt                                                          15

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      GAPDH_Fwd primer

<400> SEQUENCE: 4
ccccacacac atgcacttac c                                                   21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      GAPDH_Rev primer

<400> SEQUENCE: 5
cctagtccca gggctttgat t                                                   21

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      GAPDH_MGB probe

<400> SEQUENCE: 6
taggaaggac aggcaac                                                        17
```

NON-INVASIVE DETECTION OF FETAL GENETIC TRAITS

RELATED APPLICATIONS

This patent application is a continuation of U.S. patent application Ser. No. 13/029,999, filed on Feb. 17, 2011, entitled, NON-INVASIVE DETECTION OF FETAL GENETIC TRAITS, naming Sinuhe Hahn, Wolfgang Holzgreve, Bernhard Zimmermann and Ying Li as inventors, which is a continuation of U.S. patent application Ser. No. 10/964,726, filed on Oct. 15, 2004, now abandoned, entitled NON-INVASIVE DETECTION OF FETAL GENETIC TRAITS, naming Sinuhe Hahn, Wolfgang Holzgreve, Bernhard Zimmermann and Ying Li as inventors, which claims the benefit under 35 U.S.C. 119(a) of European Patent Application No. 03405742.2 filed on Oct. 16, 2003, issued as European Patent No. 1524321, entitled NON-INVASIVE DETECTION OF FETAL GENETIC TRAITS, naming Sinuhe Hahn, Wolfgang Holzgreve, Bernhard Zimmermann and Ying Li as inventors. The entirety of each of these patent applications is incorporated herein by reference.

SEQUENCE LISTING

The instant application contains a Sequence Listing which has been submitted electronically in ASCII format and is hereby incorporated by reference in its entirety. Said ASCII copy, created on Mar. 24, 2014, is named SEQ-5002-CT3_SL.txt and is 1,839 bytes in size.

BACKGROUND OF THE INVENTION

The presence of circulatory extracellular DNA in the peripheral blood is a well established phenomenon. In this context, it has been shown that in the case of a pregnant woman extracellular fetal DNA is present in the maternal circulation and can be detected in maternal plasma or serum. Studies have shown that this circulatory fetal genetic material can be used for the very reliable determination, e.g. by PCR (polymerase chain reaction) technology, of fetal genetic loci which are completely absent from the maternal genome. Examples of such fetal genetic loci are the fetal RhD gene in pregnancies at risk for HDN (hemolytic disease of the fetus and newborn) or fetal Y chromosome-specific sequences in pregnancies at risk for an X chromosome-linked disorder e.g. hemophilia or fragile X syndrome.

The determination of other, more complex fetal genetic loci (e.g. chromosomal aberrations such as aneuploidies or chromosomal aberrations associated with Down's syndrome, or hereditary Mendelian genetic disorders and, respectively, genetic markers associated therewith, such as single gene disorders, e.g. cystic fibrosis or the hemoglobinopathies) is, however, more problematic. The reason for this difficulty is that the major proportion (generally >90%) of the extracellular DNA in the maternal circulation is derived from the mother. This vast bulk of maternal circulatory extracellular DNA renders it difficult, if not impossible, to determine fetal genetic alternations such as those involved in chromosomal aberrations (e.g. aneuploidies) or hereditary Mendelian genetic disorders (e.g. cystic fibrosis or the hemoglobinopathies) from the small amount of circulatory extracellular fetal DNA.

SUMMARY OF THE INVENTION

An examination of circulatory extracellular fetal DNA and circulatory extracellular maternal DNA in maternal plasma has now shown that, surprisingly, the majority of the circulatory extracellular fetal DNA has a relatively small size of approximately 500 base pairs or less, whereas the majority of circulatory extracellular maternal DNA in maternal plasma has a size greater than approximately 500 base pairs. Indeed, in certain instances the circulatory DNA material which is smaller than approximately 500 base pairs appears to be almost entirely fetal. Circulatory extracellular fetal DNA in the maternal circulation has thus been found to be smaller in size (approximately 500 base pairs or less) than circulatory extracellular maternal DNA (greater than approximately 500 base pairs).

This surprising finding forms the basis of the present invention according to which separation of circulatory extracellular DNA fragments which are smaller than approximately 500 base pairs provides a possibility to enrich for fetal DNA sequences from the vast bulk of circulatory extracellular maternal DNA.

This selective enrichment, which is based on size discrimination of circulatory DNA fragments of approximately 500 base pairs or less, leads to a fraction which is largely constituted by fetal extracellular DNA. This permits the analysis of fetal genetic traits including those involved in chromosomal aberrations (e.g. aneuploidies or chromosomal aberrations associated with Down's syndrome) or hereditary Mendelian genetic disorders and, respectively, genetic markers associated therewith (e.g. single gene disorders such as cystic fibrosis or the hemoglobinopathies), the determination of which had, as mentioned above, so far proved difficult, if not impossible. Size separation of extracellular fetal DNA in the maternal circulation thus facilitates the non-invasive detection of fetal genetic traits, including paternally inherited polymorphisms which permit paternity testing.

Clinical Chemistry, 1999, Vol. 45(9), pages 1570-1572 and The Australian & New Zealand Journal of Obstetrics & Gynaecology, February 2003 (O.sub.2-2003), Vol. 43(1), pages 10-15 describe a sample of blood plasma of a pregnant woman in which extracellular fetal DNA of less than 500 base pairs is enriched by PCR, is separated by gel electrophoresis and fetal male DNA (fetal Y-chromosome-specific sequence) is detected.

The present invention provides: a fraction of a sample of the blood plasma or serum (which preferably is substantially cell-free) of a pregnant woman in which, as the result of said sample having been submitted to a size separation, the extracellular DNA present therein substantially consists of DNA comprising 500 base pairs or less; the use of such sample-fraction for the non-invasive detection of fetal genetic traits; and a process for performing non-invasive detection of fetal genetic traits which comprises subjecting a sample of the blood plasma or serum of a pregnant woman to a size separation so as to obtain a fraction of said sample in which the extracellular DNA present therein substantially consists of DNA comprising 500 base pairs or less, and determining in said sample-fraction the fetal genetic trait(s) to be detected.

Said serum or plasma sample is preferably substantially cell-free, and this can be achieved by known methods such as, for example, centrifugation or sterile filtration.

The size separation of the extracellular DNA in said serum or plasma sample can be brought about by a variety of methods, including but not limited to: chromatography or electrophoresis such as chromatography on agarose or polyacrylamide gels, ion-pair reversed-phase high performance liquid chromatography (IP RP HPLC, see Hecker K H, Green S M, Kobayashi K, J. Biochem. Biophys. Methods 2000 November 20; 46(1-2): 83-93), capillary electrophoresis in a self-coating, low-viscosity polymer matrix (see Du M, Flanagan J H Jr, Lin B, Ma Y, Electrophoresis 2003 September; 24 (18): 3147-53), selective extraction in microfabricated electrophoresis devices (see Lin R, Burke D T, Burn M A, J. Chromatogr. A. 2003 Aug. 29; 1010(2): 255-68), microchip electrophoresis on reduced viscosity polymer matrices (see Xu F, Jabasini M, Liu S, Baba Y, Analyst. 2003 June; 128(6): 589-92), adsorptive membrane chromatography (see Teeters M A, Conrardy S E, Thomas B L, Root T W, Lightfoot E N, J. Chromatogr. A. 2003 Mar. 7; 989(1): 165-73) and the like; density gradient centrifugation (see Raptis L, Menard H A, J. Clin. Invest. 1980 December; 66(6): 1391-9); and methods utilising nanotechnological means such as microfabricated entropic trap arrays (see Han J, Craighead H G, Analytical Chemistry, Vol. 74, No. 2, Jan. 15, 2002) and the like.

The sample-fraction thus obtained not only permits the subsequent determination of fetal genetic traits which had already been easily detectable in a conventional manner such as the fetal RhD gene in pregnancies at risk for HDN (hemolytic disease of the fetus and the newborn), or fetal Y chromosome-specific sequences in pregnancies at risk for an X chromosome-linked disorder such as hemophilia, fragile X syndrome or the like, but also the determination of other, more complex fetal genetic loci, including but not limited to: chromosomal aberrations (e.g aneuploidies or Down's syndrome) or hereditary Mendelian genetic disorders and, respectively, genetic markers associated therewith (e.g. single gene disorders such as cystic fibrosis or the hemoglobinopathies); and fetal genetic traits which may be decisive when paternity is to be determined.

Such determination of fetal genetic traits can be effected by methods such as, for example, PCR (polymerase chain reaction) technology, ligase chain reaction, probe hybridization techniques, nucleic acid arrays (so-called "DNA chips") and the like.

DESCRIPTION OF THE PREFERRED EMBODIMENTS

The following Examples further illustrate the invention but are not to be construed as limiting its scope in any way.

Example 1: Detection of Male Fetal DNA in Maternal Plasma by Real-Time Quantitative Polymerase Chain Reaction (PCR) After Size Fractionation of DNA by Agarose Gel Electrophoresis Materials and Methods
Subjects and Sample Processing
Seven women pregnant in the third trimester with a male fetus were recruited for this study. 16-18 ml blood samples were collected into EDTA tubes. 6-9 ml of plasma were obtained after centrifugation at 1600 g for 10 minutes and a second centrifugation of the supernatant at 16000 g for 10 minutes.
DNA Isolation
DNA from 5-7 ml plasma was extracted using the QIAgen Maxi kit, according to the manufacturers' protocol. DNA was eluted in a volume of 1.5 ml.
DNA Precipitation
1. To the plasma DNA were added: 1/10 volume NaAc (3M, pH 5.2), 2 volumes absolute ethanol, $MgCl_2$ to a final concentration of 0.01 M and Glycogen to a final concentration of 50 µg/ml. The solution was thoroughly mixed by vortexing.
2. The solution was stored overnight at −70° C.
3. The DNA was recovered by centrifugation at 20000 g for 30 minutes at 4° C.
4. The supernatant was carefully removed and the pellet washed with 500 µl 70% ethanol.
5. The pellet was air dried and dissolved in 35 µl distilled water.

DNA Separation
1. A 1% agarose Gel (Invitrogen, Cat No: 15510-027) was prepared for DNA electrophoresis.
2. 28 µl DNA solution were loaded on the gel.
3. The gel was electrophoresed at 80 Volt for 1 hour.
4. The Gel was cut into pieces corresponding to specific DNA sizes according to the DNA size markers (New England Biolabs, 100 bp ladder and Lamda Hind III digest). The DNA sizes contained by the specific gel fragments were: 90-300 bases, 300-500 bases, 500-1000 bases, 1.0-1.5 kilobases ("kb"), 1.5-23 kb and >23 kb.
5. The DNA was purified from the agarose gel pieces using the QIAEX II Gel Extraction kit (Qiagen, Cat No. 20021) and eluted in 35 µl Tris-HCl (pH 8.0, 10 mM).

Real-Time PCR
Sequences from the Y chromosome (SRY) and from chromosome 12 (GAPDH gene) were amplified with the Applied Biosystems (ABI) 7000 Sequence Detection System by real-time quantitative PCR to quantify amounts of fetal and total DNA in the size-separated fractions. The TaqMan system for SRY consisted of the amplification primers SRY_Fwd: TCC TCA AAA GAA ACC GTG CAT (SEQ ID NO: 1) and SRY_Rev: AGA TTA ATG GTT GCT AAG GAC TGG AT (SEQ ID NO: 2) and a FAM labeled TaqMan MGB (Minor Groove Binder) probe SRY_MGB: TCC CCA CAA CCT CTT (SEQ ID NO: 3). The TaqMan System for the GAPDH gene consisted of the following primers and probe: GAPDH_Fwd: CCC CAC ACA CAT GCA CTT ACC (SEQ ID NO: 4), GAPDH_Rev: CCT AGT CCC AGG GCT TTG ATT (SEQ ID NO: 5) and GAPDH_MGB: TAG GAA GGA CAG GCA AC (SEQ ID NO: 6).

TaqMan amplification reactions were set up in a total reaction volume of 25 µl, containing 6 µl of the sample DNA solution, 300 nM of each primer (HPLC purified, Mycrosynth, Switzerland) and 200 nM of each probe (ABI) at 1×concentration of the Universal PCR reaction mix (ABI). Each sample was analyzed in duplicate for each of the two amplification systems. A standard curve containing known amounts of genomic DNA was run in parallel with each analysis.

Thermal cycling was performed according to the following protocol: an initial incubation at 50° C. for 2 minutes to permit Amp Erase activity, 10 minutes at 95° C. for activation of AmpliTaq Gold, and 40 cycles of 1 minute at 60° C. and 15 seconds at 95° C.

Amplification data collected by the 7000 Sequence Detection System was quantified using the slope of the standard curve as calculated by the sequence detection software and the results of a standard DNA solution used in the dilution curve with similar DNA copy numbers as the sample reactions as a reference sample for copy number calculations.
Results
Table 1 shows that in the five pregnancies examined, DNA fragments originating from the fetus were almost completely of sizes smaller than 500 base pairs with around 70% being of fetal origin for sizes smaller than 300 bases.

These results demonstrate that free DNA of fetal origin circulating in the maternal circulation can be specifically enriched by size separation of the total free DNA in the maternal blood. Depending on the downstream application the DNA size chosen for the enrichment of fetal DNA will be smaller than 300 or smaller than 500 bases.

TABLE 1

| Size of DNA | % of fetal DNA in each fragment | % of maternal DNA in each fragment |
| --- | --- | --- |
| <0.3 kb | 73.2 (22.22-87.06) | 26.8 (12.94-77.78) |
| 0.3-0.5 kb | 18.95 (6.43-31.42) | 81.05 (68.58-93.57) |
| 0.5-1 kb | 2.81 (0.00-7.75) | 97.19 (92.25-100) |
| 1.0-1.5 kB | 0.00 (0.00-12.50) | 100 (87.5-100) |
| 1.5-23 kb | 0.00 (0.00-8.40) | 100 (100-100) |

The abbreviation "kb" appearing in the first column of this table stands for 1000 base pairs, and the figures given in its second and the third column are the median values of the percentages and, in brackets, the ranges.

Example 2: Detection of Fetal DNA After Agarose Gel Electrophoresis by Polymerase Chain Reaction (PCR) of Microsatellite Markers, also Called "Short Tandem Repeats" (STRs)

Materials and Methods

Subjects and Samples 18 ml blood samples from pregnant women and 9 ml blood from their partners were collected into EDTA tubes and plasma separated by centrifugation as described in Example 1. The maternal buffy coat (i.e. the white colored top layer of the cell pellet obtained after the first centrifugation of 1600 g for 10 min.) was washed twice with PBS.

DNA Isolation

DNA from the plasma was extracted using a modification of the High Pure DNA template kit from Roche, the whole sample was passed through the filter usually used for 200 µl using a vacuum. The DNA was eluted in a volume of 50 µl elution buffer.

Paternal DNA was extracted from 400 µl paternal whole blood, using the High Pure DNA template kit, and eluted into 100 µl. Maternal DNA was isolated from the buffy coat, using the High Pure DNA template kit, and eluted into 100 µl.

DNA Separation

The DNA was size-separated by electrophoresis on an agarose gel and purified as described in Example 1.

PCR Specific for Short Tandem Repeats

From the fraction of sizes smaller than 500 bases, sequences from tetranucleotide repeat markers on Chromosome 21 were amplified in a multiplex PCR reaction as described in Li et al. Clinical Chemistry 49, No. 4, 2003. Because of the low concentration of plasma DNA, the fetal DNA in maternal plasma was examined by using a semi-nested PCR protocol.

The maternal and paternal pairs were genotyped using total genomic DNA to monitor microsatellite markers on chromosome 21.

The STR markers used were:

D211 S11;

D21S1270;

D21S1432; and

D21S1435

The resulting DNA fragments were then size separated by capillary electrophoresis on a sequencer, and the peak areas representing each allele for a specific marker were measured by the software.

Results

TABLE 2

Detection of fetal alleles specific for the microsatellite marker (Short Tandem Repeat) D21S11 on chromosome 21

| | Maternal alleles detected (D21S11) | Fetal alleles detected (D21S11) |
| --- | --- | --- |
| Maternal genomic DNA | 232 bp<br>234 bp | N/A |
| Total extracellular DNA (unseparated) | 232 bp<br>234 bp | No fetal alleles detectable |
| Size-separated extracellular DNA (<300 bp) | 232 bp<br>234 bp | 228 bp<br>232 bp |
| Size-separated extracellular DNA (300-500 bp) | 232 bp<br>234 bp | 228 bp<br>232 bp |

Only in the size-separated fractions (<300 bp and 300-500 bp) could the fetal alleles for D21 S11 be detected, namely the paternally inherited 228 bp allele and the maternally inherited 232 bp allele, i.e., one allele from each parent.

Discussion

Analysis of the STR fragments can allow for the detection of paternal alleles that are distinct in length from the maternal repeat sequences, and by calculating the ratios between the peak areas it can be possible to identify patterns that are not consistent with a normal fetal karyotype. The identification of paternal allele sizes of STRs in the maternal circulation can allow the detection of certain chromosomal aberrations non-invasively. Also paternity testing can be accomplished prenatal in a non-invasive manner.

What is claimed is:

1. A method, comprising:
   (a) extracting DNA comprising maternal and fetal DNA fragments from a substantially cell-free sample of blood plasma or blood serum of a pregnant human female;
   (b) producing a fraction of the DNA extracted in (a) by:
      (i) size discrimination of extracellular circulatory fetal and maternal DNA fragments, and
      (ii) selectively removing the DNA fragments greater than approximately 300 base pairs,
   wherein the DNA fraction after (b) comprises extracellular circulatory fetal and maternal DNA fragments of approximately 300 base pairs and less and a plurality of genetic loci of the extracellular circulatory fetal and maternal DNA fragments; and
   (c) analyzing DNA fragments in the fraction of DNA produced in (b).

2. The method of claim 1, wherein the DNA extracted in (a) is from a substantially cell-free sample of blood plasma.

3. The method of claim 1, wherein the DNA extracted in (a) is from a substantially cell-free sample of blood serum.

4. The method of claim 1, wherein step (b) comprises chromatography.

5. The method of claim 4, wherein the chromatography comprises high performance liquid chromatography.

6. The method of claim 1, wherein step (b) comprises electrophoresis.

7. The method of claim 6, wherein the electrophoresis comprises capillary electrophoresis.

8. The method of claim 1, wherein the size discrimination in (b) comprises centrifugation.

9. The method of claim 8, wherein the centrifugation includes density gradient centrifugation.

10. The method of claim 1, wherein the size discrimination in (b) comprises nanotechnological means.

11. The method of claim 1, wherein the analyzing comprises using nucleic acid arrays.

12. The method of claim 1, wherein analyzing DNA fragments in the fraction of DNA produced in (b) is by a process comprising detection of a fetal chromosome aberration.

13. The method of claim 12, wherein the fetal chromosome aberration is an aneuploidy.

14. The method of claim 12, wherein the fetal chromosome aberration causes Down's syndrome.

* * * * *